(12) United States Patent
Burba et al.

(10) Patent No.: US 11,460,480 B2
(45) Date of Patent: *Oct. 4, 2022

(54) METHODS AND APPARATUS FOR MEASURING GAS FLUX

(71) Applicant: Li-Cor, Inc., Lincoln, NE (US)

(72) Inventors: George G. Burba, Lincoln, NE (US); Dayle McDermitt, Lincoln, NE (US); Xiaomao Lin, Lincoln, NE (US); Liukang Xu, Lincoln, NE (US); Dave Johnson, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 953 days.

This patent is subject to a terminal disclaimer.

(21) Appl. No.: 16/058,480

(22) Filed: Aug. 8, 2018

(65) Prior Publication Data

US 2018/0372770 A1    Dec. 27, 2018

Related U.S. Application Data

(63) Continuation of application No. 13/441,319, filed on Apr. 6, 2012, now Pat. No. 10,060,942.

(51) Int. Cl.
*G01P 5/00* (2006.01)
*G01N 33/00* (2006.01)
(Continued)

(52) U.S. Cl.
CPC .......... *G01P 5/001* (2013.01); *G01N 33/0067* (2013.01); *A61B 5/14532* (2013.01);
(Continued)

(58) Field of Classification Search
None
See application file for complete search history.

(56) References Cited

U.S. PATENT DOCUMENTS

| 5,067,356 A | 11/1991 | Businger |
| 10,060,942 B2 | 8/2018 | Burba et al. |

(Continued)

FOREIGN PATENT DOCUMENTS

| JP | 08261891 A | * 10/1996 | |
| WO | WO-2011028202 A1 | * 3/2011 | ......... G01N 21/3504 |
| WO | WO 2011/130320 A2 | 10/2011 | |

OTHER PUBLICATIONS

U.S. Appl. No. 13/441,319, filed Apr. 6, 2012.
(Continued)

*Primary Examiner* — Arleen M Vazquez
*Assistant Examiner* — Leonard S Liang
(74) *Attorney, Agent, or Firm* — Gerald T. Gray; Leydig, Voit & Mayer, LTD.

(57) ABSTRACT

Systems and methods for measuring turbulent gas flux using high-speed vertical wind speed measurements (e.g., on the order of 5-10 Hz or more frequently) and low-speed gas content measurements (e.g., on the order of 5 Hz or less frequently), without the need for the sophisticated and expensive high-speed hardware to separate gas samples (e.g., into accumulation bags) according to updrafts and downdrafts. A time series of high-speed vertical wind speed data is used as a guide to distinguish between updrafts and downdrafts. When vertical wind speed is upward (updraft), the low-speed gas content is recorded into a data structure in one location, or marked with one flag. When vertical wind speed is downward (downdraft), the low-speed gas content is recorded into a different location, or marked with a different flag. Eddy Accumulation or Relaxed Eddy Accumulation computations can be performed using the stored gas content data to determine gas flux.

24 Claims, 3 Drawing Sheets

(51) Int. Cl.
    *A61B 5/145*      (2006.01)
    *G01N 21/3504*    (2014.01)
    *G01N 30/86*      (2006.01)
    *G01W 1/10*       (2006.01)

(52) U.S. Cl.
    CPC ..... *G01N 21/3504* (2013.01); *G01N 30/8624* (2013.01); *G01W 1/10* (2013.01)

(56) References Cited

U.S. PATENT DOCUMENTS

| | | | |
|---|---|---|---|
| 2011/0054803 A1 | 3/2011 | Burba et al. | |
| 2011/0122397 A1 | 5/2011 | Wong | |
| 2012/0050750 A1 | 3/2012 | Hays et al. | |
| 2012/0092649 A1 | 4/2012 | Wong | |
| 2013/0014577 A1 | 1/2013 | Tam et al. | |
| 2013/0250304 A1 | 9/2013 | Burba | |
| 2013/0314694 A1* | 11/2013 | Tchoryk, Jr. | G01N 21/538 356/28.5 |

OTHER PUBLICATIONS

"CPEC200 Closed-Path Eddy-Covariance Flux System," Campbell Scientific, Inc. Publication, Copyright 2011, 2012, Printed Apr. 2012 (3 pages).

"EC155 CO2 and H2O Closed-Path Gas Analyzer and EC100 Electronics with Optional CSAT3A 3D Sonic Anemometer Revision: Aug. 2011 Instruction Manual," Campbell Scientific, Inc. Publication, Copyright 2010-2011 (63 pages).

Sargent, Steve and Kim, Hongcheol, "Frequency Response of a Low-Power Closed-Path CO2 and H2O Eddy Covariance System," Campbell Scientific, Inc. (1 page).

Darmais, S. et al., "Emission fluxes of VOC by orange trees determined by both relaxed eddy accumulation and vertical gradient approaches," Chemosphere: Global Change Science, (2000), vol. 2, No. 1, pp. 47-56.

Grönholm, Tiia et al., "The dependence of the β coefficient of REA system with dynamic deadband on atmospheric conditions," Environmental Polution, (2008), vol. 152, No. 3, pp. 597-603.

Ueyama, Masahito et al., "Continuous measurement of methane flux over a larch forest using a relaxed eddy accumulation method," Theoretical and Applied Climatology, (2012), vol. 109, No. 3-4, pp. 461-472.

European Search Report for European Patent Application No. 13162587.3 dated Jul. 10, 2013.

Katul et al., "An Investigation of the Conditional Sampling Method Used to Estimate Fluxes of Active ,Reactive, and Passive Scalars," 1996 American Meteorological Society, vol. 35, Journal of Applied Meteorology, Oct. 1996.

Komori et al., Development of an Air Sampling System for the True Eddy Accumulation Technique, J. Agric. Meteorol. 60 (4): 263-272, 2004.

Taipale et al., "Lag time determination in DEC measurements with PTR-MS," Atmos. Meas. Tech., 3, 853-862, 2010.

Mauder et al., "Documentation and Instruction Manual of the Eddy-Covariance Software Package TK3", Complete Manual 60 pages, May 2011.

Anctil et al., "Eddy-Correlation Measurements of Air-Sea Fluxes from a Discus Buoy," Journal of Atmospheric and Aceanic Tech., vol. 11, pp. 1144-1149, 1993.

Wolf et al., Cospectral Analysis of High Frequency Signal Loss in Eddy Covariance Measurements, p. 13151-13173, Atmospheric Chemistry and Physics Discussions, vol. 7, 2007.

Hicks et al., "A Simulation of the Eddy Accumulation Method for Measuring Pollutant Fluxes," Journal of Climate and Applied Meteorology vol. 23, pp. 637-643, Apr. 1984.

Katul et al., "Sensible and Latent Heat Flux Predictions Using Conditional Sampling Methods," Water Resources Research, vol. 30, No. 11, pp. 3053-3059, Nov. 1994.

* cited by examiner

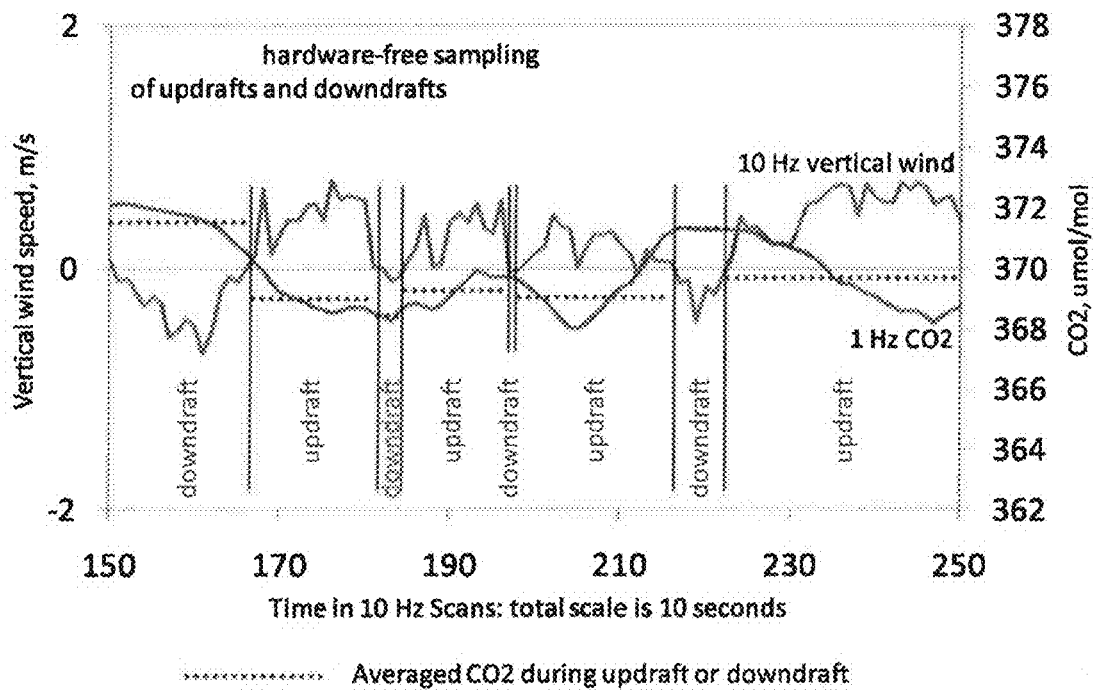
FIG. 3
FIG. 4
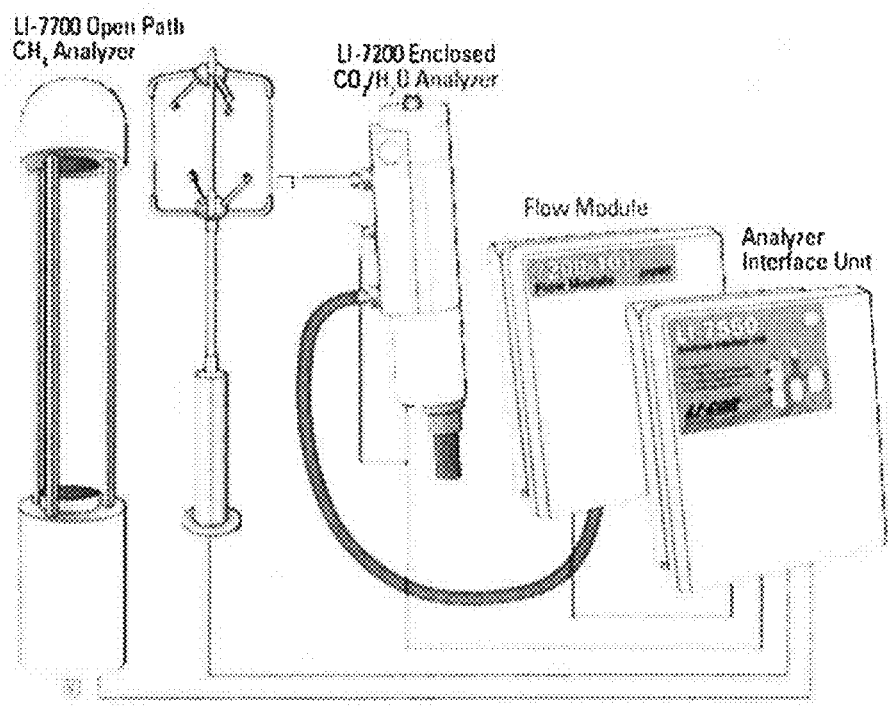

METHODS AND APPARATUS FOR MEASURING GAS FLUX

CROSS-REFERENCES

The present Application for Patent is a continuation of U.S. patent application Ser. No. 13/441,319 by Burba et al., entitled "Methods and Apparatus to Measuring Gas Flux," filed Apr. 6, 2012, which is fully incorporated herein by reference.

BACKGROUND

The present embodiments relate generally to systems and methods for measuring gas flux, and more particularly to systems and methods for measuring turbulent gas flux.

The increasing concentrations of carbon dioxide and other traces gases (e.g. $H_2O$, $CH_4$, $N_2O$, $NH_3$, etc.) in the atmosphere and the resulting greenhouse effect and climate change have become important topics for scientific research. In order to understand the global carbon balance, it is necessary to determine the rate at which carbon dioxide and energy exchanges between the atmosphere and terrestrial and oceanic ecosystems. The air within a few hundred meters above the earth's surface is mostly turbulent, so that turbulent structures (vortices of variable sizes) called "eddies" are responsible for the vertical transport of most of the gases, including carbon dioxide and water vapor, and also heat and momentum between the surface and the atmosphere. The rates of such transport can be calculated from simultaneous, high-frequency measurements of the vertical component of wind speed, the concentrations of carbon dioxide and water vapor, and the air temperature.

Currently, there are three main methods for computing turbulent gas flux rates, typically performed from towers, airplanes and other platforms: these are Eddy Covariance, Eddy Accumulation, and Relaxed Eddy Accumulation methods.

The Eddy Covariance (EC) method is the most direct and reliable method for gas flux measurements available to date. EC is a dominating method used in most turbulent flux measurements. EC is used as a standard for other turbulent flux measurement methods, and for any atmospheric flux measurement methods. However, EC requires high-speed gas concentration measurements (e.g., 5-10 Hz or more) in addition to the high-speed vertical wind speed measurements (e.g., 5-10 Hz or more). However, high-speed gas concentration measurement devices are expensive, and they do not exist for a number of gas species.

The Eddy Accumulation (EA) method is theoretically as reliable as EC, and it also requires high-speed vertical wind speed measurements, but it does not require high-speed gas concentration measurements. However, EA does need a highly sophisticated high-speed wind sampling system to distinguish updrafts from downdrafts, and another highly sophisticated high-speed system to sample gas into accumulation bags in proportion to the rates of the updrafts and downdrafts. Such systems performing at satisfactory levels are not presently available (see, e.g., Foken, T., 2009, Micrometeorology).

The Relaxed Eddy Accumulation (REA) method is a version of EA which does not require sampling in proportion to the rate of the updrafts and downdrafts. However, REA does also require a sophisticated high-speed wind sampling system to distinguish updrafts from downdrafts, while sampling into the accumulation bags is done at a constant flow rate. REA is not able to measure fluxes as reliably as EC or EA due to an empirical parameter required for calculations, but REA is used occasionally for measuring fluxes of gas species for which no high-speed gas measurement devices are available. Both the EA and the REA methods also have built-in measurement uncertainties associated with system configurations and components such as valve systems, sampling delays, tube time delays and attenuation, etc.

Therefore it is desirable to provide systems and methods that overcome the above and other problems.

BRIEF SUMMARY

The present embodiments include systems and methods for measuring gas flux, and more particularly systems, methods and devices for measuring turbulent gas flux using high-speed vertical wind speed measurements (e.g., on the order of 5-10 Hz or more) and low-speed gas content (e.g., density or concentration) measurements (e.g., on the order of 5 Hz or less), without the need for the sophisticated and expensive high-speed hardware to separate gas samples (e.g., into accumulation bags) according to updrafts and downdrafts. Gas flux measurements are useful for measuring or estimating heat, water and $CO_2$ exchange as well as methane and other trace gases.

Various embodiments use the mathematical concepts of EA and REA analysis methods, but advantageously do not need or use sampling hardware associated with these methods. Instead of using high-speed components, e.g., valves and bags, to physically separate and accumulate air samples during wind updrafts from those during wind downdrafts, various embodiments use a time series of high-speed vertical wind speed data as a guide to distinguish between updrafts and downdrafts, which is typically done during data post-processing. For the time when vertical wind is upward (updraft), the low-speed gas content (e.g., density or concentration) is recorded into one location, or marked with one flag. For the time when vertical wind is downward (downdraft), the low-speed gas content is recorded into a different location, or marked with a different flag. Thus, gas content of the updrafts can be characterized separately from the downdrafts without high-speed components such as valves and bags, while the rest of the methodology and mathematical operations remain substantially the same, or similar, as in the EA or REA methods.

According to one embodiment, a method is provided for measuring gas flux of a target gas in a system having a wind speed measurement device and a gas analyzer. The method typically includes obtaining vertical wind speed data using the wind speed measurement device, the vertical wind speed data including a plurality a vertical wind speed measurements (W) obtained over a period of time at a sampling rate of about 5 Hz or greater. The method also typically includes obtaining gas content data using the gas analyzer, the gas content data including a plurality of gas content measurements of the target gas obtained over said period of time at an effective sampling rate of about 5 Hz or less. The method further typically includes aligning the plurality of vertical wind speed measurements data with the plurality of gas content measurements data based on time, and determining, from the plurality of vertical wind speed measurements, updraft time periods when the wind speed has an upward component and downdraft time periods when the wind speed has a downward component. The method further typically includes identifying, for each of the updraft time periods and the downdraft time periods, a gas content measurement corresponding to said time period, determining an average or integrated gas content value for the updraft time periods (this average gas content value is denoted $C\uparrow$) and an average or integrated gas content value for the downdraft time periods (this average gas content value is denoted $C\downarrow$), and determining a gas flux (F) of the target gas using the values $C\uparrow$ and $C\downarrow$. In certain aspects, the target gas is $CO_2$. Other target gases might include $H_2O$, $CH_4$, $N_2O$, $NH_3$, etc., including various isotopes.

In certain aspects, the gas flux (F) is determined using an equation of the form:

$$F=\beta\sigma_w(C\uparrow-C\downarrow),$$

wherein $\sigma_w$ is a standard deviation of W, or other similar statistical parameter describing variation (e.g., squared variance, etc.), and wherein $\beta$ is an empirical value.

In certain aspects, the method further includes determining an average or integrated wind speed value for the updraft time periods (this average wind speed value is denoted $W\uparrow$) and an average or integrated wind speed value for the downdraft time periods (this average wind speed value is denote $W\downarrow$). In certain aspects, the gas flux (F) is determined using an equation of the form:

$$F=\beta\sigma_w(C\uparrow-C\downarrow),$$

wherein $\sigma_w$ is a standard deviation of W, or other similar statistical parameter describing variation (e.g., squared variance, etc.), and wherein $\beta=\sigma_w/(W\uparrow-W\downarrow)$. In certain aspects, determining an average gas content value ($C\uparrow$) includes multiplying each gas content measurement corresponding to an updraft time period by the average vertical wind speed for that updraft time period to produce updraft values, normalizing each updraft value by the average or integrated wind speed value ($W\uparrow$), and averaging all normalized updraft values to produce the average gas content value ($C\uparrow$).

In certain aspects, determining an average gas content value ($C\downarrow$) includes multiplying each gas content measurement corresponding to a downdraft time period by the average vertical wind speed for that downdraft time period to produce downdraft values, normalizing each downdraft value by the average or integrated wind speed value ($W\downarrow$), and averaging all normalized downdraft values to produce the average gas content value ($C\downarrow$). In certain aspects, the gas flux (F) is determined using an equation of the form:

$$F=W\uparrow C\uparrow-W\downarrow C\downarrow.$$

According to another embodiment, a system is provided for measuring gas flux of a target gas. The system typically includes a wind speed measurement device configured to obtain vertical wind speed data including a plurality a vertical wind speed measurements (W) obtained over a period of time at a sampling rate of about 5 Hz or greater, and a gas analyzer configured to obtain gas content data including a plurality of gas content measurements of the target gas obtained over said period of time at an effective sampling rate of about 5 Hz or less. The system also typically includes an intelligence module adapted to receive the vertical wind speed data and the gas content data, wherein the intelligence module is configured to align the plurality of vertical wind speed measurements with the plurality of gas content measurements based on time, and to determine, from the plurality of vertical wind speed measurements (W), updraft time periods when the wind speed has an upward component and downdraft time periods when the wind speed has a downward component. The intelligence module is also configured to identify, for each of the updraft time periods and the downdraft time periods, a gas content measurement corresponding to said time period, to determine an average or integrated gas content value for the updraft time periods (this average gas content value is denoted $C\uparrow$) and an average or integrated gas content value for the downdraft time periods (this average gas content value is denoted $C\downarrow$); and to determine a gas flux (F) of the target gas using the values $C\uparrow$ and $C\downarrow$. In certain aspects, the target gas is $CO_2$. Other target gases might include $H_2O$, $CH_4$, $N_2O$, $NH_3$, etc., including various isotopes.

In certain aspects, the intelligence module determines the gas flux (F) using an equation of the form:

$$F=\beta\sigma_w(C\uparrow-C\downarrow),$$

wherein $\sigma_w$ is a standard deviation of W, or other similar statistical parameter describing variation (e.g., squared variance, etc.), and wherein $\beta$ is an empirical value.

In certain aspects, the intelligence module is also configured to determine an average or integrated wind speed value for the updraft time periods (this average wind speed value is denoted $W\uparrow$) and an average or integrated wind speed value for the downdraft time periods (this average wind speed value is denoted $W\downarrow$). In certain aspects, the intelligence module determines the gas flux (F) using an equation of the form:

$$F=\beta\sigma_w(C\uparrow-C\downarrow),$$

wherein $\sigma_w$ is a standard deviation of W, or other similar statistical parameter describing variation (e.g., squared variance, etc.), and wherein $\beta=\sigma_w/(W\uparrow-W\downarrow)$. In certain aspects, the intelligence module determines an average gas content value ($C\uparrow$) by multiplying each gas content measurement corresponding to an updraft time period by the average vertical wind speed for that updraft time period to produce updraft values, by normalizing each updraft value by the average or integrated wind speed value ($W\uparrow$), and by averaging all normalized updraft values to produce the average gas content value ($C\uparrow$).

In certain aspects, the intelligence module determines an average gas content value ($C\downarrow$) by multiplying each gas content measurement corresponding to a downdraft time period by the average vertical wind speed for that downdraft time period to produce downdraft values, by normalizing each downdraft value by the average or integrated wind speed value ($W\downarrow$), and by averaging all normalized downdraft values to produce the average gas content value ($C\downarrow$). In certain aspects, the intelligence module determines the gas flux (F) using an equation of the form:

$$F=W\uparrow C\uparrow-W\downarrow C\downarrow.$$

The various embodiments advantageously allow for computing turbulent gas flux using mathematical concepts of EA and REA, but without the use of sophisticated and expensive sampling hardware associated with these methods. For gas species for which no high-speed gas measurement devices are available, the embodiments advantageously provide ways of computing turbulent gas flux using direct measurements of turbulent flux transport. For gas species for which high-speed gas measurement devices are available, the embodiments advantageously provide substantially more cost-effective ways of computing turbulent gas flux, because low-speed gas measurement devices are usually considerably less expensive than high-speed gas measurement devices.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 3 illustrates an example of sampling of updrafts separately from downdrafts using 10 Hz time series of vertical wind speed and 1 Hz time series of gas content ($CO_2$); actual field data during midday in September: vertical wind speed is from a sonic anemometer, and $CO_2$ content is from a LI-7200 gas analyzer.

FIG. 4 illustrates a specific gas flux measuring system including a sonic anemometer positioned proximal to an open-path gas analyzer and also proximal to a closed-path gas analyzer.

Figure 1:
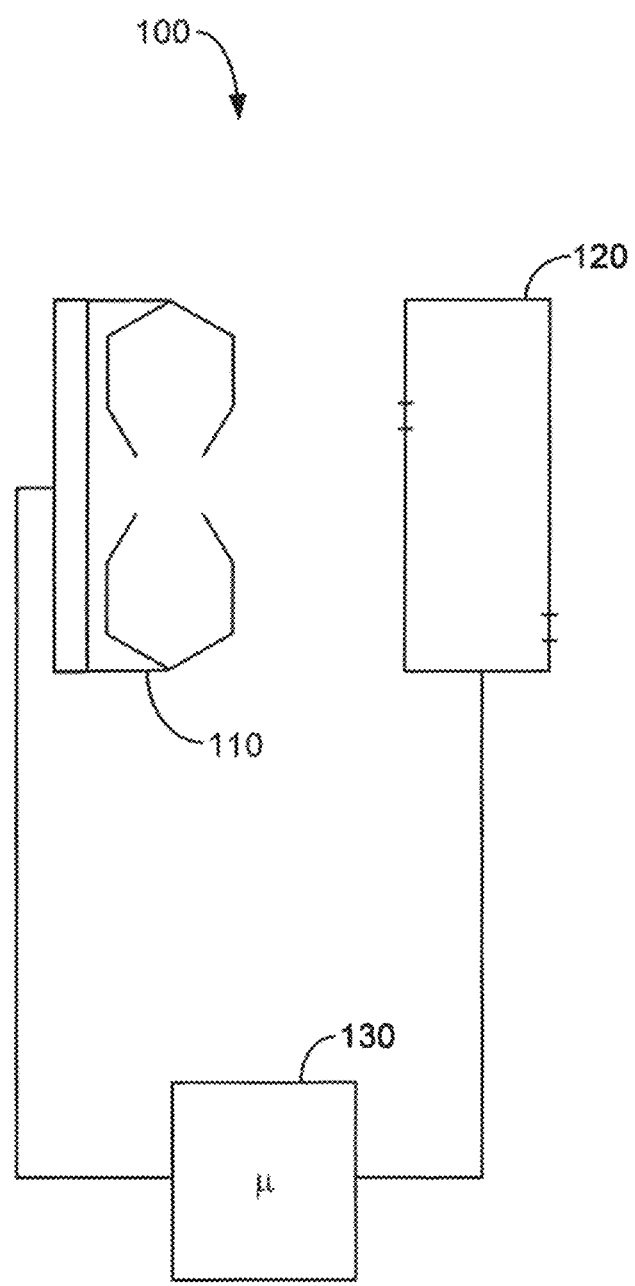
FIG. 1 illustrates a gas flux measurement system according to one embodiment.

The patent or application file contains at least one drawing executed in color. Copies of this patent or patent application publication with color drawing(s) will be provided by the U.S Patent and Trademark Office upon request and payment of the necessary fee.

DETAILED DESCRIPTION

The present embodiments provide systems and methods for measuring gas flux, and in particular systems and methods for measuring turbulent gas flux. Gas flux measurements are useful for measuring or estimating heat, water and $CO_2$ exchange, as well as exchange of methane and other trace gases.

Various embodiments use Eddy Accumulation and Relaxed Eddy Accumulation paradigms to perform flux computations without the need for the sophisticated and expensive high-speed hardware to separate gas samples according to updrafts and downdrafts.

1. Eddy Accumulation

Using the traditional Eddy Accumulation (EA) method, turbulent gas flux is computed as follows:

$$F=C{\uparrow}W{\uparrow}-C{\downarrow}W{\downarrow}, \quad [1]$$

where F is gas flux, $C{\uparrow}$ is the averaged gas content of samples accumulated into an updraft bag, $C{\downarrow}$ is the averaged gas content of samples accumulated into a downdraft bag, $W{\uparrow}$ is the average speed of updrafts, and $W{\downarrow}$ is the average speed of downdrafts. In operation, $C{\uparrow}$ is collected into the updraft bag only during updrafts, and is collected with the sampling flow proportional to the updraft rate. Similarly, $C{\downarrow}$ is collected into the downdraft bag only during downdrafts, and is collected with the sampling flow proportional to the downdraft rate. Traditionally, EA requires a high-speed device (including valves, solenoids, etc.) and related electronics that need to operate with extremely high-speed and accuracy to distinguish between updrafts and downdrafts, which often change at rate of about 10 Hz (10 times a second) or greater. The high-speed sampling device (such as a pump, or blower and sampling bags) and related electronics have to be extremely high-speed and sensitive to be able to sample at a rate proportional to the vertical wind speed, which changes sign very fast, and has generally low magnitudes, e.g., of about 0.01-2.0 m/s. As a result, no acceptable device was yet been made, and the EA method is used rarely, and then only for short time periods (see, e.g., Foken, T., 2009, Micrometeorology).

2. Relaxed Eddy Accumulation

Using the traditional Relaxed Eddy Accumulation (REA) method, turbulent gas flux is computed as follows:

$$F=\beta\sigma_w(Q{\uparrow}-Q{\downarrow}), \quad [2]$$

where F is the gas flux, $\beta$ is an empirical coefficient (Katul et al. (1994) uses $\beta=\Box\sigma_w/(W{\uparrow}-W{\downarrow})$), $\sigma_w$ is the standard deviation of W, the vertical wind speed over a given period of time, or other similar statistical parameter describing variation (e.g., squared variance, etc.), $Q{\uparrow}$ is the averaged gas content of samples accumulated into an updraft bag, $Q{\downarrow}$ is the averaged gas content of samples accumulated into a downdraft bag, $W{\uparrow}$ is the average speed of updrafts, and $W{\downarrow}$ is the average speed of downdrafts. In operation, $Q{\uparrow}$ is collected into the updraft bag only during updrafts, and is collected with the constant sampling flow rate (not proportional to the updraft rate). Similarly, $Q{\downarrow}$ is collected into the downdraft bag only during downdrafts, and is collected with the constant sampling flow rate (not proportional to the downdraft rate). Traditionally, REA requires a high-speed device (including valves, solenoids, etc.) and related electronics that have to operate with extremely high-speed and accuracy to distinguish between updrafts and downdrafts, which often change at a rate of about 10 Hz (10 times a second) or greater. Also, the coefficient $\beta$ is highly variable and is not always predictable. Nevertheless, the REA method is used much more often than the EA method, likely because the hardware needed is easier to make and operate.

FIG. 1 illustrates a gas flux measurement system 100 according to one embodiment. Gas Flux measurement system 100 includes a vertical wind speed measurement device 110 and a gas content measurement device 120. A control module 130 is coupled with the wind speed measurement device 110 and the gas content measurement device 120. In certain aspects, control module 130 includes an intelligence module such as a processor or computer system that provides control signals to vertical wind speed measurement device 110 and gas content measurement device 120 as necessary, and that receives data and other signals from vertical wind speed measurement device 110 and gas content measurement device 120. In certain aspects, control module 130 is configured with logic to perform the data collection and flux calculation processing functionality based on signals received from the wind speed measuring device 110 and the gas content measurement device 120 as described herein. It should be understood that the control module 130 could be a separate device as shown or could be integrated with one of wind speed measurement device 110 or gas content measurement device 120. It should also be understood that control module 130 may be configured to merely collect and store the data and that the collected data may be transmitted to, sent to, or otherwise provided to a separate system that implements the data processing and flux computation functionality described herein.

In one embodiment, vertical wind speed measurement device 110 includes a sonic anemometer for measuring vertical wind speed at a sampling rate of about 5 Hz or greater. However, vertical wind speed measurement device 110 may includes any device suitable for measuring vertical wind speed at a sampling rate of about 5 Hz or greater. Other useful wind speed measuring devices include hot film anemometers, ionization anemometers, laser anemometers, scintillometers, sonar devices and others. Gas content measurement device 120 includes any device suitable for measuring gas content of a desired target gas at a sampling rate of about 5 Hz or less. For example, in one embodiment, the gas content measurement device 120 includes a gas analyzer (e.g., an open-path or a closed-path gas analyzer). Useful gas analyzers include NDIR based analyzers, laser based analyzers, chemical-based analyzers, etc. Specific useful gas analyzers include the LI-7200 gas analyzer and the LI-7500 gas analyzer, both from LI-COR Biosciences, Lincoln, Nebr. U.S. Pat. Nos. 6,317,212, 6,369,387, 8,125,626 and 8,130,379, which are each hereby incorporated by reference in its entirety, disclose various useful features of open and closed path gas analyzers. In certain aspects, the gas content measurement device has an effective sampling rate of about 5 HZ or less frequently. For example, one can use a slow device, e.g., with time response of 1 Hz and sample this slow signal at 20 Hz, however, the effective sampling rate is limited by the slow device at 1 Hz.

FIG. 4 shows a picture of a specific gas flux measuring system including a sonic anemometer positioned proximal to an open-path gas analyzer and also proximal to a closed-path gas analyzer according to one embodiment. A control module ("Analyzer Interface Unit") coupled with the anemometer and the gas analyzers is also shown.

Gas flux computations based on the EA concept or the REA concept and based on data collected using system 100 are implemented in various embodiments. In certain embodiments, rather than collecting gas, C (or Q), into actual bags using actual high-speed sampling devices, a high-speed time series of wind speed measurements (W) is used to determine when updrafts or downdrafts have occurred and a low-speed time series of gas concentration or content measurements are used to determine the gas content during the particular updraft or downdraft periods.

Figure 2:
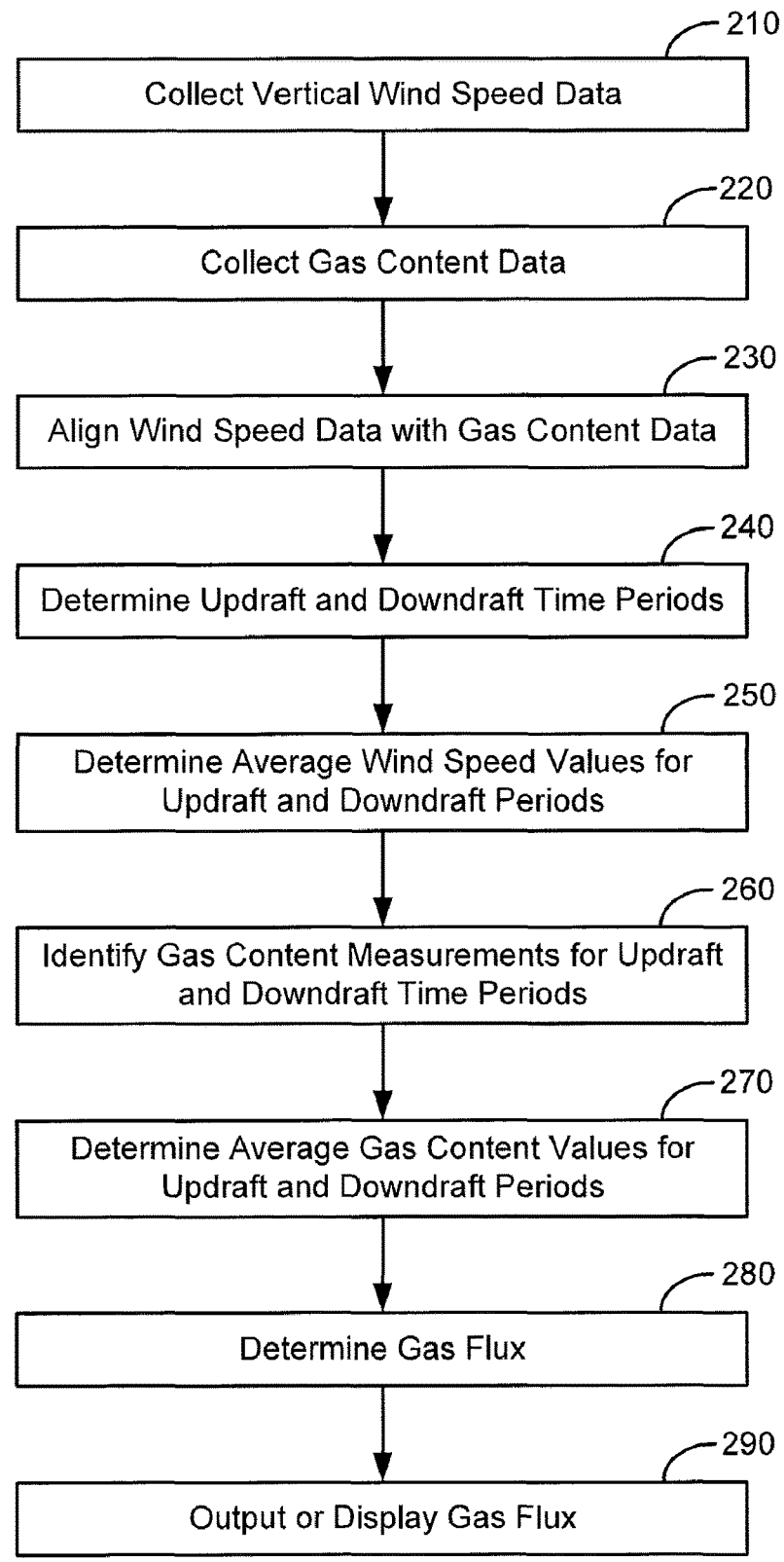
FIG. 2 illustrates a process of measuring gas flux according to one embodiment.

FIG. 2 illustrates a process 200 of measuring gas flux according to one embodiment. In step 210, vertical wind speed data is collected over a given time period using wind speed measuring device 110. The time period over which the data is collected can be an arbitrary or a predetermined time period and can last as little as a few seconds or for hours (e.g., 10 seconds, or 1 minute, or 20 minutes, or 1 hour, or 12 hours, etc.) or longer. In certain aspects, the wind speed data is collected at a sampling rate of about 5 Hz or greater (e.g., 5 Hz, or 8 Hz, or 10 Hz, or 20 Hz or more frequently). In step 220, gas content data is collected simultaneously, or nearly simultaneously, with the collection of the wind speed data for the given time period using gas content measuring device 120. In certain aspects, the gas content data is collected at a sampling rate of about 5 Hz or less (e.g., 5 Hz, or 2 Hz, or 1 Hz or less frequently).

In step 230, the wind speed data is aligned with the gas content data, e.g., to compensate for any timing differences or delays in signal acquisition from the gas content and wind speed measurement devices. For example, where a sonic anemometer is used in close proximity to a closed-path gas analyzer, air sampled by the sonic anemometer may arrive at the intake of the gas analyzer some time later (e.g., on the order of a fraction of a second, a second or several seconds later depending on how close the intake of the gas analyzer may be to the anemometer, how long the intake tube is, and how fast is the flow of the sampled gas in the tube). For an open-path gas analyzer, the air sampled by the sonic anemometer may not arrive at the optical measuring region of the analyzer for some time, depending on the distance between the anemometer and the analyzers, wind speed and direction. If such delays are not corrected, fluctuations in the vertical wind speed may not correlate with the gas concentration, and the flux may be underestimated. In certain aspects, alignment calculations include applying a circular correlation process to the data (e.g., by shifting the delay scan by scan until a maximum flux correlation is identified).

In certain aspects, alignment calculations include applying a time delay computation based on one or more physical parameters of the system, such as for example parameters that impact flow rate in the gas analysis system, the set-up configuration of the system (e.g., position of wind speed measurement device 110 relative to gas content measurement device 120), the wind speed, the wind direction, frequency response characteristics of the instruments, etc. Physical parameters that might impact the flow rate in the gas analysis system include the physical dimensions of the flow tube such as a diameter and length of the flow tube flow rate in the tube, tube surface roughness, temperature and humidity, and stickiness of the sampled gas. It should be appreciated that the vertical wind speed measurement device 110 and the gas content measurement device 120 should be in close proximity to each other to facilitate better alignment and more robust data correlation. For example, it is desired that the vertical wind speed measurement device (e.g., sonic anemometer) be placed or located in close proximity to the intake of the gas measurement device (e.g., intake opening or tube of a gas analyzer). Other components of the system (e.g., intelligence or control module 130) need not be in close proximity to the measurement components.

The time alignment of the high-speed vertical wind speed time series data with low-speed gas content time series data may be done using circular correlation when there is enough fluctuation in both time series to compute the R-square. When no R-square can be computed with confidence, tube flow rate measurements or estimates may be required to compute time delay in the sampling tube of the closed-path gas analyzer. For an open-path gas analyzer, time delay may be computed from the distance between the anemometer and the analyzer, and wind speed and direction.

In step 240, updraft time periods and downdraft time periods are determined from the vertical wind speed measurement data. In certain aspects, downdraft time periods are defined as those periods of time when the vertical wind speed is downward (e.g., negative values), and updraft time periods are defined as those periods of time where the vertical wind speed is upward (e.g., positive values). In certain aspects, for a given time period, an average vertical wind speed is determined from the collected wind speed data, and updraft time periods are defined as those periods of time when the vertical wind speed exceeds the average vertical wind speed, and downdraft time periods are defined as those periods of time where the wind speed is below the average vertical wind speed. In certain aspects, before the vertical wind speed is averaged, a coordinate rotation process or algorithm as is well known may be applied to the data to make sure that the vertical wind component is not contaminated with horizontal wind components (e.g., as may occur if the wind speed measuring device is not appropriately vertically aligned). The time period over which the average vertical wind speed is determined may be the same as or different than the time period over which the vertical wind speed data were collected. For example, where the vertical wind speed measurements may have been collected over the course of 20 minutes, the average vertical wind speed could be determined for the entire 20 minute time span of collected wind speed data, or the average vertical wind speed could be determined for different intervals within the 20 minute time span of collected wind speed data (e.g., 4×300 second intervals or 6×200 second intervals, etc.).

In (optional) step 250, average wind speed values are determined for the updraft and downdraft time periods. For example, in one embodiment, the averaged or integrated vertical wind speed value (W↑) for updraft time periods is determined by taking the average vertical wind speed of all updraft time periods; similarly, the averaged or integrated vertical wind speed value (W↓) for downdraft time periods is determined by taking the average vertical wind speed of all downdraft time periods.

In step 260, gas content measurements are identified for each of the updraft and downdraft time periods. In certain embodiments, for each period of updrafts and downdrafts, the respective gas concentration or content is determined and stored to a data structure so as to distinguish between updrafts and downdrafts. In one embodiment, data is recorded in separate places for updrafts than for downdrafts. In certain aspects, for example, this is done by storing data to a table or spreadsheet with two columns, one for updraft gas content, and one for downdraft gas content. Alternatively, gas content data can be flagged separately for updraft and downdraft periods. Other means or methods for separately recording, or for marking gas content data differently for updraft and downdraft time periods would also be suitable. Gas content and vertical wind speed data alignment step 230 facilitates determining gas content data associated with the updraft and downdraft time periods. It should be appreciated that data alignment step 230 need not be done prior to step 240 or step 250.

In step 270, average gas content values are determined for the updraft and downdraft time periods. For example, in one embodiment, the averaged or integrated gas content value (C↑) for updraft time periods is determined by taking the average of the gas content values for all updraft time periods; similarly, the averaged or integrated gas content value (C↓) for downdraft time periods is determined by taking the average of the gas content values for all downdraft time periods.

In step 280, the gas flux is calculated or determined. In certain embodiments, gas flux is determined using the values C↓ and C↑. In some embodiments, gas flux is determined using the values C↓, C↑, W↓, and W↑. Depending on the specific calculation methodology desired, e.g., EA or REA, the actual gas flux calculation will vary as discussed below. In step 290, the gas flux is displayed, e.g., displayed on a monitor or other display device or printed via a printer on a tangible medium, or otherwise recorded or output for further use or display. For example, the gas flux measurement, as well as other data, may be sent to another system for further processing and/or recording via electronic transmission over a wired or wireless network, via distribution by portable storage media, or otherwise.

For REA calculations, in one embodiment, the gas flux (F) is determined using an equation of the form $F=\beta\sigma_w(C\uparrow - C\downarrow)$, where $\sigma_w$ is the standard deviation of W, i.e., the standard deviation of the wind speed over the given measurement time period, or other similar statistical parameter describing variation (e.g., squared variance, etc.). In certain aspects, $\beta=\sigma_w/(W\uparrow - W\downarrow)$. In certain other aspects, the parameter β has an empirical value in the range of about 0.4 to about 0.8. One particular empirical β value from literature of 0.6 can be used. Alternatively, β can be determined in any other suitable manner. It should be appreciated that step 250 process 200 (FIG. 1) is optional when the REA method is to be used with an empirical value for β. Otherwise, step 250 should be implemented to facilitate REA and EA computations.

For EA calculations, in one embodiment, the gas flux (F) is determined using an equation of the form $F=W\uparrow C\uparrow - W\downarrow C\downarrow$. For EA calculations, in certain aspects, determining an average gas content value C↑ (e.g., in step 270) includes multiplying each gas content measurement corresponding to an updraft time period by the average vertical wind speed for that updraft time period to produce updraft values, normalizing each updraft value by the average or integrated wind speed value (W↑), and averaging all normalized updraft values to produce the average gas content value C↑, similarly, determining an average gas content value C↓ (e.g., in step 270) includes multiplying each gas content measurement corresponding to a downdraft time period by the average vertical wind speed for that downdraft time period to produce downdraft values, normalizing each downdraft value by the average or integrated wind speed value (W↓), and averaging all normalized downdraft values to produce the average gas content value C↓.

FIG. 3 illustrates an example of a display of data sampled according to one embodiment. Sampling of updrafts was collected and recorded separately from downdrafts using 10 Hz time series of vertical wind speed and 1 Hz time series of gas content ($CO_2$). FIG. 3 was generated using actual field data collected during midday in September 2010: vertical wind speed is from a sonic anemometer, and $CO_2$ content is from a LI-7200 gas analyzer.

The efficacy of an embodiment was tested using a high-speed time series of vertical wind speed data collected by a sonic anemometer (CSAT3, CSI, Logan, Utah), and using a low-speed time series of $CO_2$ mole fraction collected by a gas analyzer (LI-7200, LI-COR, Lincoln, Nebr.). The reference values for $CO_2$ flux were computed by the Eddy Covariance method using the time series data from the sonic anemometer and from the LI-7200. High-speed gas data from LI-7200 were converted into low-speed data using run-mean averaging to emulate averaging times of 1 second (1 Hz), 2 seconds (0.5 Hz), and 10 seconds (0.1 Hz). Fluxes were computed using algorithms for EA and REA described herein above, and compared to the reference fluxes from Eddy Covariance. In addition to the straight-forward calculations using the entire range of all available high-speed data for vertical wind, fluxes were also computed for periods excluding very small magnitudes of the vertical wind speed, as customarily done in the REA method to avoid uncertainties associated with small W. Results of all comparisons are shown in Table I:

TABLE I

Performance of the embodiment for EA and REA concepts compared to Eddy Covariance reference. Data were collected during midday at 2.1 m height over ryegrass in September. Vertical wind speed was always measured at 10 Hz. The exclusion threshold for W was computed as $\sigma_w$ divided by the product of gas analyzer frequency (1.0, 0.5, and 0.1 Hz) and sonic anemometer frequency (10 Hz).

| Gas analyzer frequency | EC | EA Concept without W exclusion | EA Concept with W exclusion | REA Concept without W exclusion | REA Concept with W exclusion |
|---|---|---|---|---|---|
| 10 Hz | −0.582 100% | <--- reference standard | | | |
| 1 Hz | −0.507 87% | −0.542 93% | −0.590 101% | −0.563 97% | −0.627 108% |
| 0.5 Hz | −0.445 76% | −0.476 82% | −0.566 97% | −0.504 87% | −0.621 103% |
| 0.1 Hz | −0.253 43% | −0.386 66% | −0.577 99% | −0.294 51% | −0.449 77% |

As seen from the Table I, using a low-speed gas analyzer degrades results of the reference Eddy Covariance method from 100% to 43% when the analyzer is slowed from 10 Hz to 0.1 Hz. This is expected, because Eddy Covariance methods require both the sonic anemometer and the gas analyzer to be high-speed (5-10 Hz sampling rate or greater). At the same time, using the embodiment achieves results considerably better than the reference Eddy Covariance method, when the gas analyzer is low-speed. Both the EA and REA concepts performed better than Eddy Covariance method for the low-speed gas analyzer. When the response of the low-speed gas analyzer is 1 Hz, or when exclusion of small vertical wind speeds is applied for analyzers at 0.5 Hz and 0.1 Hz, the embodiment using a low-speed gas analyzer performs similar to the reference Eddy Covariance method with a high-speed gas analyzer, The application of the above embodiments to real field data demonstrates the efficacy of computing turbulent fluxes using low-speed gas time series measurements and high-speed vertical wind speed time series measurements without physically separating the updraft and downdraft samples.

It should be appreciated that the gas flux determination processes described herein may be implemented in processor executable code running on one or more processors. The code includes instructions for controlling the processor(s) to implement various aspects and steps of the gas flux determination processes. The code is typically stored on a hard disk, RAM or portable medium such as a CD, DVD, etc. The processor(s) may be implemented in a control module of a gas flux measurement system, or in a different component of the system such as gas analyzer having one or more processors executing instructions stored in a memory unit coupled to the processor(s). The processor(s) may be part of a separate system directly or indirectly coupled with the gas flux measurement system. Code including such instructions may be downloaded to the system or gas analyzer memory unit over a network connection or direct connection to a code source or using a portable, non-transitory computer-readable or processor-readable medium as is well known.

One skilled in the art should appreciate that the processes of the present invention can be coded using any of a variety of programming languages such as C, C++, C#, Fortran, VisualBasic, etc., as well as applications such as Mathematica® which provide pre-packaged routines, functions and procedures useful for data visualization and analysis. Another example of the latter is MATLAB®.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A method of measuring gas flux in a gas flux measurement system comprising a control system communicably coupled with a wind speed measurement device and a gas analyzer positioned proximal to the wind speed measurement device, the method comprising:

obtaining vertical wind speed data from the wind speed measurement device, the vertical wind speed data including a plurality of vertical wind speed measurements (W) obtained over a period of time at a wind speed sampling rate of about 5 Hz or greater;

storing the plurality of vertical wind speed measurements (W) to a memory unit of the control system, wherein each of the plurality of wind speed measurements (W) includes a vertical wind speed data value sampled at each time interval corresponding to the wind speed sampling rate;

obtaining gas content data using from the gas analyzer, the gas content data including a plurality of gas content measurements obtained by the gas analyzer over said period of time at an effective gas content sampling rate of between about 0.01 Hz and 5 Hz, wherein the gas content data is obtained by the gas analyzer without using bags or valves to collect gas prior to the gas content measurements being obtained;

storing the plurality of gas content measurements to the memory unit, wherein each of the plurality of gas content measurements includes a gas content data value sampled at each time interval corresponding to the gas content sampling rate;

aligning the plurality of vertical wind speed measurements with the plurality of gas content measurements based on time;

determining, from the plurality of vertical wind speed measurements (W), updraft time periods when the wind speed has an upward component and downdraft time periods when the wind speed has a downward component;

identifying, for each of the updraft time periods and the downdraft time periods, a gas content measurement corresponding to said time period;

determining an average or integrated gas content value (C↑) for the updraft time periods and an average or integrated gas content value (C↓) for the downdraft time periods; and determining a gas flux (F) using the values C↑ and C↓.

2. The method of claim 1, wherein the gas flux (F) is determined using an equation of the form:

$$F=\beta\sigma_w(C\uparrow-C\downarrow),$$

wherein $\sigma_w$ is a standard deviation of W, or other similar statistical parameter describing variation, and wherein $\beta$ is an empirical value.

3. The method of claim 2, wherein $\beta$ has a value of between about 0.4 and about 0.8.

4. The method of claim 1, further including determining an average or integrated wind speed value (W↑) for the updraft time periods and an average or integrated wind speed value (W↓) for the downdraft time periods.

5. The method of claim 4, wherein determining an average gas content value (C↑) includes:

multiplying each gas content measurement corresponding to an updraft time period by the average vertical wind speed for that updraft time period to produce updraft values;

normalizing each updraft value by the average or integrated wind speed value (W↑); and averaging all normalized updraft values to produce the average gas content value (C↑);

wherein determining an average gas content value (C↓) includes:

multiplying each gas content measurement corresponding to a downdraft time period by the average vertical wind speed for that downdraft time period to produce downdraft values;

normalizing each downdraft value by the average or integrated wind speed value (W↓); and averaging all normalized downdraft values to produce the average gas content value (C↓); and wherein the gas flux (F) is determined using an equation of the form:

$$F=\overline{W{\uparrow}C{\uparrow}-W{\downarrow}C{\downarrow}}.$$

6. The method of claim 4, wherein the gas flux (F) is determined using an equation of the form:

$$F=\beta\sigma_w(C{\uparrow}-C{\downarrow}),$$

wherein $\sigma_w$ is a standard deviation of W, or other similar statistical parameter describing variation, and wherein $\beta=\sigma_w/(W{\uparrow}-W{\downarrow})$.

7. The method of claim 4, wherein determining average or integrated wind speed values W↑ and W↓ includes determining a total average or integrated wind speed for said period of time.

8. The method of claim 1, wherein aligning includes applying a time delay computation to align the plurality of vertical wind speed measurements with the plurality of gas content measurements based on one or more of a physical parameter of the gas analyzer, wind speed, wind direction, and system setup configuration.

9. The method of claim 1, wherein identifying gas content measurements corresponding to said updraft and downdraft time periods includes flagging stored gas content measurements differently in the memory unit for updraft and downdraft time periods.

10. The method of claim 1, wherein identifying gas content measurements corresponding to said updraft and downdraft time periods includes storing, in the memory unit, gas content measurements corresponding to an updraft time period in a different column or logically separate location in a database table than gas content measurements corresponding to a downdraft time period.

11. The method of claim 1, further including applying a coordinate rotation process to the vertical wind speed data to remove horizontal wind speed components.

12. The method of claim 1, wherein aligning includes applying a circular correlation process to align the plurality of vertical wind speed measurements with the plurality of gas content measurements or computing time alignment from wind speed and direction and distance between devices.

13. The method of claim 1, further including storing the gas flux (F) to the memory unit.

14. A system for measuring gas flux; the system comprising:
a wind speed measurement device configured to obtain vertical wind speed data including a plurality of vertical wind speed measurements (W) obtained over a period of time at a wind speed sampling rate of greater than about 5 Hz;
a gas analyzer positioned proximal to the wind speed measurement device, the gas analyzer configured to obtain gas content data including a plurality of gas content measurements obtained over said period of time at an effective gas content sampling rate of 0.01 Hz to 5 Hz, wherein the gas content data is obtained without using bags or valves to collect gas prior to the gas content measurements being obtained; and
a control module including a processor, wherein the control module is adapted to receive the vertical wind speed data and the gas content data, wherein each of the plurality of wind speed measurements (W) includes a vertical wind speed data value sampled at each time interval corresponding to the wind speed sampling rate, wherein each of the plurality of gas content measurements includes a gas content data value sampled at each time interval corresponding to the gas content sampling rate, and wherein the processor is configured to:
align the plurality of vertical wind speed measurements with the plurality of gas content measurements based on time;
determine, from the plurality of vertical wind speed measurements (W), updraft time periods when the wind speed has an upward component and downdraft time periods when the wind speed has a downward component;
identify, for each of the updraft time periods and the downdraft time periods, a gas content measurement corresponding to said time period;
determine an average or integrated gas content value (C↑) for the updraft time periods and an average or integrated gas content value (C↓) for the downdraft time periods; and
determine a gas flux (F) using the values C↑ and C↓.

15. The system of claim 14, wherein the processor is configured to determine the gas flux F using an equation of the form:

$$F=\beta\sigma_w(C{\uparrow}-C{\downarrow}),$$

wherein $\sigma_w$ is a standard deviation of W, or other similar statistical parameter describing variation, and wherein β is an empirical value.

16. The system of claim 15, wherein β has a value of between about 0.4 and about 0.8.

17. The system of claim 14, wherein the processor is further configured to determine an average or integrated wind speed value (W↑) for the updraft time periods and an average or integrated wind speed value (W↓) for the downdraft time periods.

18. The system of claim 17, wherein the processor is configured to determine an average gas content value C↑ by:
multiplying each gas content measurement corresponding to an updraft time period by the average vertical wind speed for that updraft time period to produce updraft values;
normalizing each updraft value by the average or integrated wind speed value (W↑); and
averaging all normalized updraft values to produce the average gas content value (C↑);
wherein the processor is configured to determine an average gas content value (C↓) by:
multiplying each gas content measurement corresponding to a downdraft time period by the average vertical wind speed for that downdraft time period to produce downdraft values;
normalizing each downdraft value by the average or integrated wind speed value (W↓); and
averaging all normalized downdraft values to produce the average gas content value (C↓); and
wherein the processor is configured to determine the gas flux (F) using an equation of the form:

$$F=\overline{W{\uparrow}C{\uparrow}-W{\downarrow}C{\downarrow}}.$$

19. The system of claim 17, wherein the processor is configured to determine the gas flux F using an equation of the form:

$$F=\beta\sigma_w(C{\uparrow}-C{\downarrow}),$$

wherein $\sigma_w$ is a standard deviation of W, or other similar statistical parameter describing variation, and wherein $\beta=\sigma_w/(W{\uparrow}-W{\downarrow})$.

20. The system of claim 17, wherein the processor is further configured to determine a total average or integrated wind speed for said period of time.

21. The system of claim 14, wherein the processor is configured to identify gas content measurements corresponding to said updraft and downdraft time periods by flagging, in a memory unit, stored gas content measurements differently for updraft and downdraft time periods.

22. The system of claim 14, wherein the processor is further configured to store the gas flux (F) to a memory unit.

23. A computer-implemented method of measuring gas flux, the method comprising steps, performed by a processor coupled with a memory unit, of:

retrieving, from the memory unit, vertical wind speed data, the vertical wind speed data including a plurality of vertical wind speed measurements (W) having been obtained by a wind speed measurement device over a period of time at a wind speed sampling rate of about 5 Hz or greater, wherein each of the plurality of wind speed measurements (W) includes a vertical wind speed data value sampled at each time interval corresponding to the wind speed sampling rate;

retrieving, from the memory unit, gas content data, the gas content data including a plurality of gas content measurements having been obtained by a gas analyzer positioned proximal to the wind speed measurement device over said period of time at an effective gas content sampling rate of between about 0.01 Hz and 5 Hz, wherein the gas content data having been obtained by the gas analyzer without using bags or valves to collect gas prior to the gas content measurements being obtained, wherein each of the plurality of gas content measurements includes a gas content data value sampled at each time interval corresponding to the gas content sampling rate;

aligning the plurality of vertical wind speed measurements with the plurality of gas content measurements based on time;

determining, from the plurality of vertical wind speed measurements (W), updraft time periods when the wind speed has an upward component and downdraft time periods when the wind speed has a downward component;

identifying, for each of the updraft time periods and the downdraft time periods, a gas content measurement corresponding to said time period;

determining an average or integrated gas content value (C↑) for the updraft time periods and an average or integrated gas content value (C↓) for the downdraft time periods; and determining a gas flux (F) using the values C↑ and C↓.

24. The computer-implemented method of claim 23, further comprising the step, performed by the processor, of storing the gas flux (F) to the memory unit.

* * * * *